United States Patent [19]
Yapp et al.

[11] Patent Number: 5,616,144
[45] Date of Patent: Apr. 1, 1997

[54] OSTEOSYNTHESIS PLATE SYSTEM

[75] Inventors: Ronald A. Yapp, Marshfield; Charles B. Worrick, III, Hanson, both of Mass.

[73] Assignee: Codman & Shurtleff, Inc., Randolph, Mass.

[21] Appl. No.: 468,635

[22] Filed: Jun. 6, 1995

Related U.S. Application Data

[60] Continuation of Ser. No. 234,240, Apr. 28, 1994, abandoned, which is a division of Ser. No. 981,281, Nov. 25, 1992, abandoned.

[51] Int. Cl.$^6$ ............................. A61B 17/70; A61B 17/80
[52] U.S. Cl. ................................................ 606/61; 606/69
[58] Field of Search ................................. 606/69–71, 60, 606/61, 65, 66, 53

[56] References Cited

U.S. PATENT DOCUMENTS

| Re. 28,841 | 6/1976 | Allgower et al. . | |
|---|---|---|---|
| 556,642 | 3/1896 | Reessing . | |
| 872,897 | 12/1907 | Chapman et al. . | |
| 1,084,680 | 1/1914 | Wegener . | |
| 1,907,506 | 5/1933 | Coburn . | |
| 1,980,336 | 11/1934 | Hoagland | 82/30 |
| 3,741,205 | 6/1973 | Markolf et al. | 128/92 B |
| 4,003,376 | 1/1977 | McKay et al. | 128/69 |
| 4,219,015 | 8/1980 | Steinemann | 606/69 |

(List continued on next page.)

FOREIGN PATENT DOCUMENTS

| 0201024 | 4/1986 | European Pat. Off. . | |
|---|---|---|---|
| 0242842 | 4/1987 | European Pat. Off. . | |
| 0410309A1 | 1/1991 | European Pat. Off. | A61B 17/56 |
| 1505513 | 11/1967 | France | 606/99 |
| 2435243 | 5/1980 | France | 606/69 |
| 2708704 | 9/1977 | Germany | 606/89 |
| 186085 | 12/1966 | U.S.S.R. . | |
| 1424824 | 9/1988 | U.S.S.R. | A61B 17/58 |
| WO92/118189 | 7/1992 | WIPO . | |
| 092011819 | 7/1992 | WIPO | 606/61 |

OTHER PUBLICATIONS

Page 1/2 and 2/2—sheets of drawings from Canadian Patent #1112803.
"Techniques of Screw Fixation of the Cervical Spine", Dickman et al., *BNI Quarterly* 8:2 (Spring 1992), pp. 9–26.
"Anatomic and Biomechanical Study of Posterior Cervical Spine Plate Arthrodesis: An Evaluation of Two Different Techniques of Screw Placement", Montesano et al., *J. Spinal Disorders* 5:3 (1992), pp. 301–305.
"Lateral Mass Posterior Plating and Facet Fusion for Cervical Spinal Instability", Cherny, et al., *BNI Quarterly* 7:2 (Spring 1991), pp. 2–11.

*Primary Examiner*—Robert A. Hafer
*Assistant Examiner*—Brian E. Hanlon
*Attorney, Agent, or Firm*—William C. Geary, III; Nutter, McClennen & Fish, LLP

[57] ABSTRACT

An osteosynthesis plate system is particularly well adapted to securely fuse adjacent cervical vertebrae. The plates are for mounting upon the anterior or posterior surfaces of the vertebrae. Plates for mounting on the anterior vertebral surfaces have a concave bone contacting surface and a bone screw locking mechanism integral with each screw hole. Moreover, the bone contacting surface of the plate has a plurality of bone penetrating protrusions to more securely affix the plate to bone. Plates for mounting on the posterior vertebral surfaces also have bone penetrating protections on their bone contacting surfaces. Such plates are formed so as to have a curved bone contacting surface that is concave in the transverse axis of the plate and convex in the longitudinal axis of the plate. The screw holes of such plates are constructed so as to guide a bone screw along a desired angle to improve the anchoring of the screws in bone.

6 Claims, 9 Drawing Sheets

U.S. PATENT DOCUMENTS

| | | | |
|---|---|---|---|
| 4,388,921 | 6/1983 | Sutter et al. | |
| 4,484,570 | 11/1984 | Sutter et al. | |
| 4,493,317 | 1/1985 | Klaue | 606/69 |
| 4,503,848 | 3/1985 | Caspar et al. | |
| 4,762,122 | 8/1988 | Slocum | 606/70 |
| 4,794,918 | 1/1989 | Wolter | 128/92 YP |
| 4,836,196 | 6/1989 | Park et al. | 606/61 |
| 4,943,292 | 7/1990 | Foux | 606/70 |
| 5,002,544 | 3/1991 | Klaue et al. | |
| 5,041,113 | 8/1991 | Biedermann et al. | 606/71 X |
| 5,053,036 | 10/1991 | Perren et al. | 606/71 X |
| 5,057,111 | 10/1991 | Park | 606/69 |
| 5,085,660 | 2/1992 | Lin | |
| 5,102,412 | 4/1992 | Rogozinski | 606/61 |
| 5,108,395 | 4/1992 | Laurain | 606/73 X |
| 5,127,914 | 7/1992 | Calderale et al. | 606/65 |
| 5,129,899 | 7/1992 | Small et al. | 606/61 |
| 5,133,717 | 7/1992 | Chopin | 606/61 |
| 5,147,360 | 9/1992 | Dubousset | 606/61 |
| 5,147,361 | 9/1992 | Ojima et al. | 606/69 X |
| 5,151,103 | 9/1992 | Tepic et al. | 606/61 |
| 5,180,381 | 1/1993 | Aust et al. | 606/61 |
| 5,234,431 | 8/1993 | Keller | 606/69 X |
| 5,257,994 | 11/1993 | Lin | 606/61 |
| 5,261,910 | 11/1993 | Warden et al. | 606/61 |
| 5,300,073 | 4/1994 | Ray et al. | 606/61 |
| 5,395,371 | 3/1995 | Miller et al. | 606/61 |

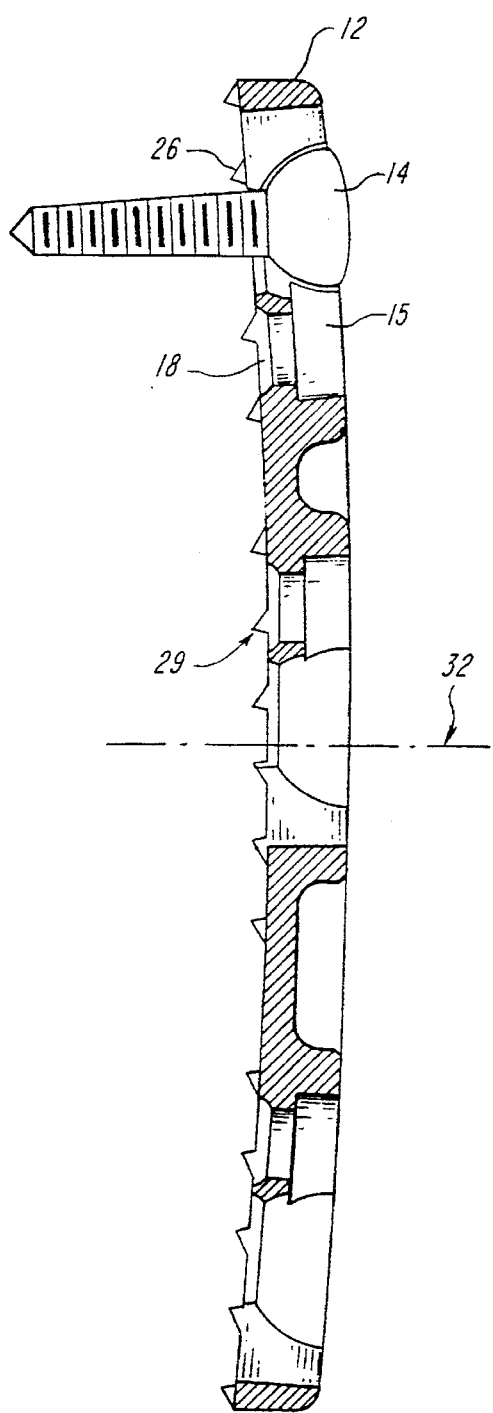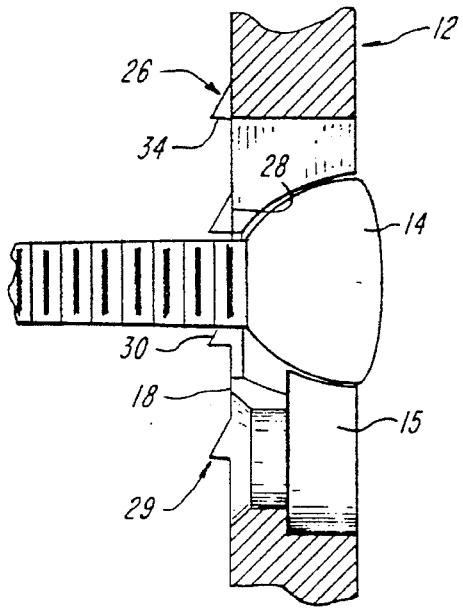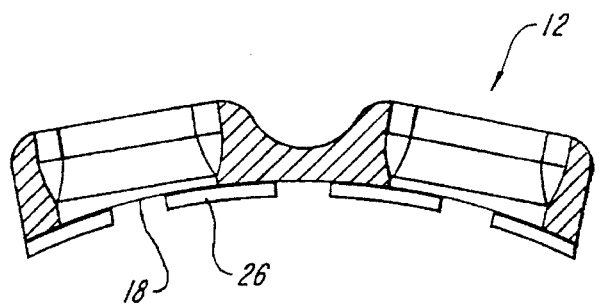
FIG. 4
FIG. 4A
FIG. 5

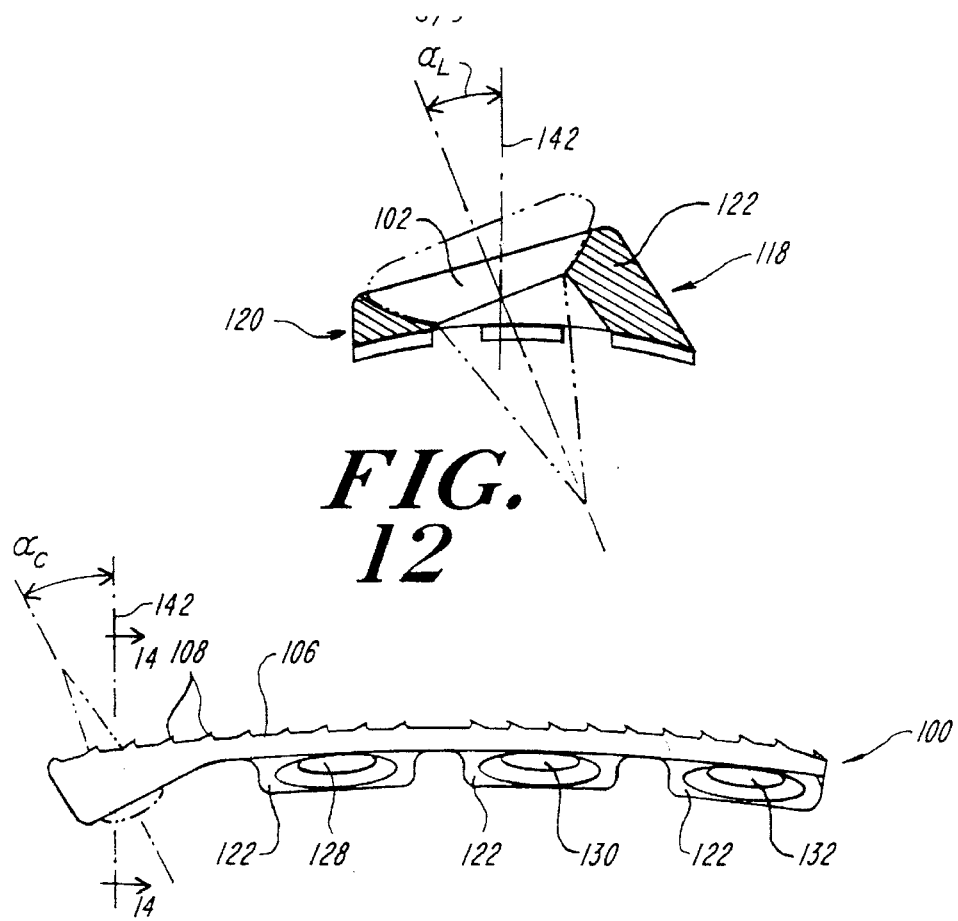
FIG. 12
FIG. 13A
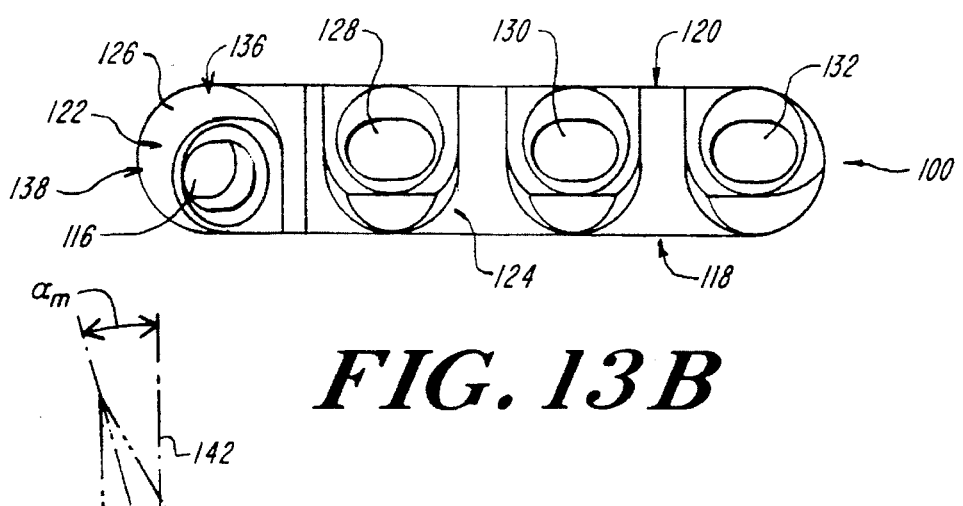
FIG. 13B
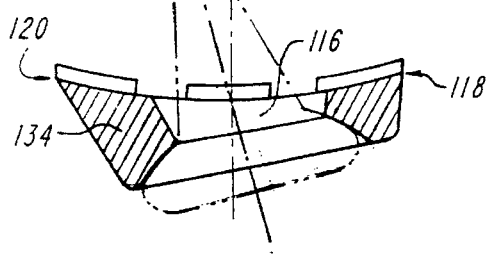
FIG. 14

OSTEOSYNTHESIS PLATE SYSTEM

This application is a continuation of application Ser. No. 08/234,240 filed on Apr. 28, 1994, now abandoned, which is a divisional of application Ser. No. 07/981,281 filed on Nov. 25, 1992 now abandoned.

BACKGROUND OF THE INVENTION

This invention relates to osteosynthesis plates, and more particularly to such plates useful to immobilize adjacent vertebral bodies.

Proper healing of injured or damaged skeletal parts requires immobilization of the injured skeletal segments to ensure the proper growth of new osseous tissue between the segments. Insufficient immobilization can compromise the healing process and may result in further complications or injury.

Osteosynthesis plates have been used to immobilize adjacent skeletal parts such as bones. Typically, a rigid plate is positioned to span bones or bone segments that must be immobilized with respect to one another. The plate is fastened to the bone, for example with bone screws, so that the plate remains in contact with the bone and that the bones or bone segments are immobilized.

Such plates have been used to immobilize a variety of bones, and have recently been adapted for use in fusing and immobilizing adjacent vertebral bodies. The morphology of spinal bone presents unique challenges to the design of effective osteosynthesis plates for fusing vertebral bodies. Among the challenges involved in fusing vertebral bodies is the effective installation of a plate that will resist migration despite the rotational and translational forces it faces. For a plate to work effectively in such an environment, screws must be properly positioned and anchored within the bone. Several known plate designs use elongate, slotted openings for screw placement in the plate. While useful in providing freedom of positioning screws, this contributes to the potential for slippage between the plate and screw head along the longitudinal axis of the plate. Such plates have also been designed to conform to the shape of vertebral bodies which they contact.

Despite the existence of osteosynthesis plate systems adapted for use in fusing vertebral bodies, there remains a need for an osteosynthesis plate system that is able to be securely installed between adjacent bones or bone segments, particularly vertebral bodies.

It is thus an object of the invention to provide an osteosynthesis plate system which maximizes immobilization of adjacent bones or bone segments. Another object is to provide such a system adapted for use in fusing adjacent vertebral bodies. A further object is to provide an osteosynthesis plate system for placement on the anterior surface of vertebral bodies to immobilize two or more adjacent vertebrae. It is also an object to provide an osteosynthesis plate system for placement on the posterior surface of vertebral bodies to immobilize two or more adjacent vertebrae. Another object is to provide such plate systems able to be more securely affixed to bone. Other objects will be apparent upon review of the disclosure that follows.

SUMMARY OF THE INVENTION

The present invention provides an osteosynthesis plate system that effectively immobilizes adjacent bones or bone segments, and which has improved plate rigidity and securement to bone. The plate system of the present invention is well adapted for use in fusing adjacent vertebral bodies, particularly vertebrae in the cervical spine.

The plate system of the present invention comprises a rigid, elongate plate member which is adapted to bridge or immobilize adjacent bones or bone segments.

In one aspect of the invention the osteosynthesis plate system is adapted to mount on the anterior surface of vertebral bodies to bridge and immobilize two or more adjacent vertebral bodies. The plate system comprises an elongate plate member having a plurality of substantially circular screw holes that extend through the member. Each screw hole has a substantially spherical seat that is adapted to seat bone screws having a spherical head to allow infinite degrees of freedom in the angular orientation of the screw. The bone contacting surface of the plate preferably includes a number of bone penetrating projections that are adapted to penetrate the bone as a result of compression forces induced by fixing the plate to the bone with bone screws. Preferably, the flat regions of the plate lie flush against the bone when the plate is properly installed.

The plate system also includes a locking mechanism that is integral with the plate member and adjacent one or more of the screw holes. The locking mechanism functions to secure the bone screw to the plate member to inhibit axial and rotational movement of the bone screws seated within the screw holes and anchored in bone. The locking mechanism may comprise a rotatable cam mounted in the member adjacent one or more of the screw holes. The cam preferably has a ovoid shape and is rotatable so as to engage a surface of a screw head seated in a screw hole adjacent to the cam such that axial and rotational movement of the screw is inhibited. Alternatively, the locking mechanism may comprise a deflectable arm that forms a portion of a screw hole seat, and a cam mounted in the member adjacent the deflectable arm. The cam is rotatable such that upon rotation it imparts a force to the deflectable arm causing the arm to exert a radial force on the screw head to inhibit rotational and axial movement to the screw.

In another embodiment the plate system of the invention is specially adapted to be mounted upon the posterior surface of two or more vertebral bodies, particularly in the cervical spine. The plate member has one surface which contacts the bone, and another surface which faces away from the bone. Disposed within the plate are at least two, spaced apart screw holes having substantially spherical countersinks, each of which is adapted to receive a bone screw. Preferably, the screw holes are aligned with each other about the longitudinal axis of the plate member. In a preferred embodiment the screw holes are oriented at desired angles with respect to the longitudinal and transverse axes of the plate member to ensure proper positioning of the bone screw within the hole, and thus the proper angular trajectory of the screw into the bone. The bone contacting surface of the plate member includes a plurality of projections, each of which is adapted to penetrate the cortical layer of bone to improve the bone/plate interface. Compression forces which result from the use of screws in fixing the plate to the bone will cause the projections to penetrate the bone such that flat areas of the bone contacting surface are substantially flush with the bone.

BRIEF DESCRIPTION OF THE DRAWINGS

FIG. 4 is a longitudinal sectional view along lines B—B of the plate shown in FIG. 3.

FIG. 4A is a detail view of a portion of the plate shown in FIG. 4.

FIG. 5 is a transverse sectional view, along lines D—D of the plate shown in FIG. 3.

FIG. 12 is a sectional view along lines 12—12 of the plate illustrated in FIG. 10A.

FIG. 13A is a side view of a posterior osteosynthesis plate of the present invention adapted for use at cervical vertebrae 2 and below.

FIG. 13B is a view of the non-bone contacting surface of the plate of FIG. 13A.

FIG. 14 is a sectional view along lines 14—14 of the plate of FIG. 13A.

DESCRIPTION OF THE INVENTION

The osteosynthesis plates of the invention are useful for fixing and immobilizing adjacent bones and/or bone segments. The plates are best adapted for use in fusing adjacent vertebrae, particularly the cervical vertebrae. The plates are adapted to mount either on the anterior or posterior surface of the vertebrae, preferably secured to the vertebrae by bone screws. The plates are intended to immobilize the adjacent skeletal segments to promote healing. As a result of such immobilization new osseous tissue will grow between the adjacent segments, resulting in fusing of the segments.

Figure 1:
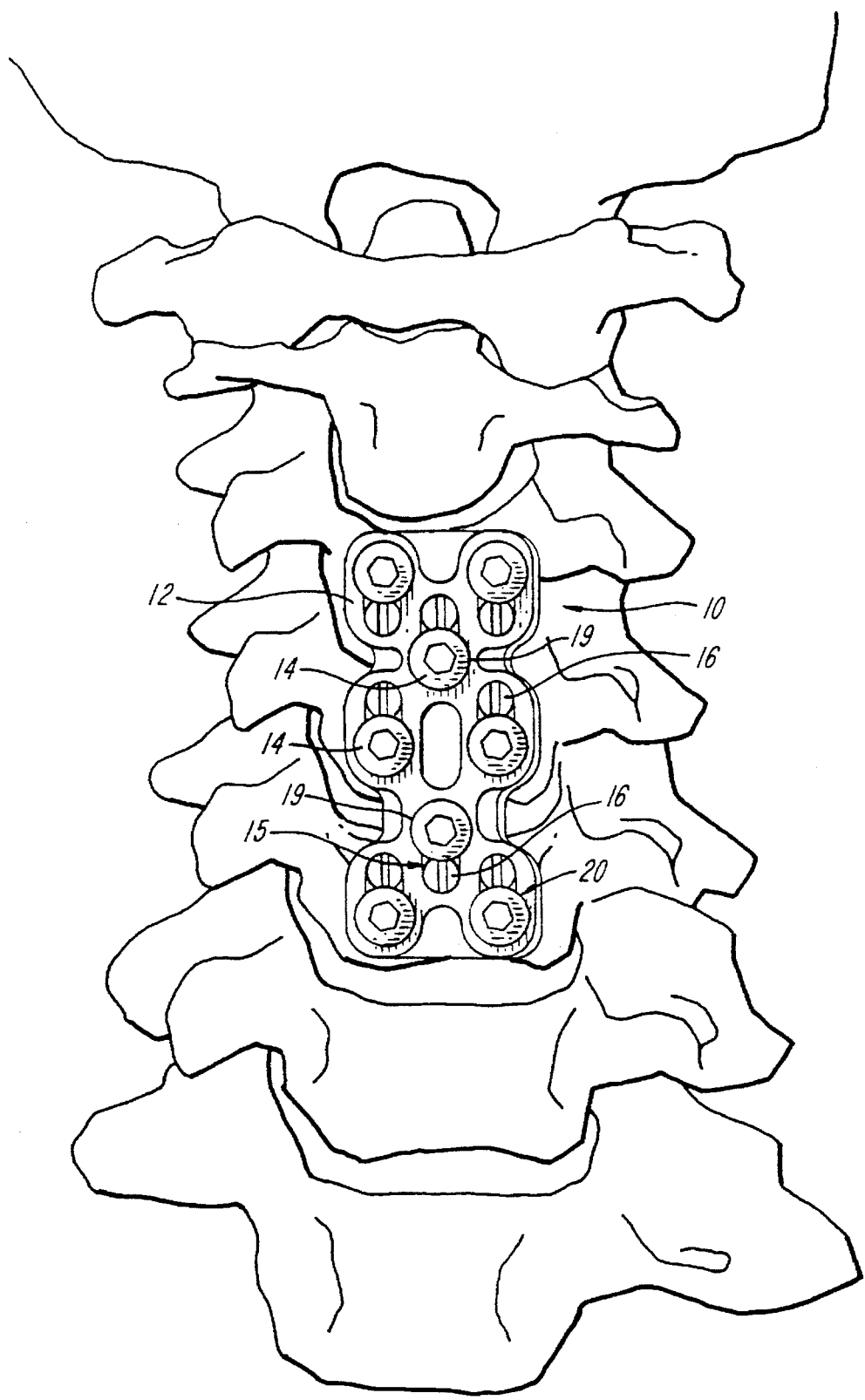
FIG. 1 illustrates an anterior osteosynthesis plate of the present invention affixed to the anterior surface of the cervical spine.

FIG. 1 illustrates an osteosynthesis plate system 10 adapted to be affixed to the anterior surface of the cervical spine. The system 10 comprises an anterior osteosynthesis plate 12 having positioned therein a number of bone screws 14 that extend through screw holes 19, 20 in the plate to allow the screws 14 to compress the plate against the bone when anchored in bone. The bone screws 14 may be secured in the plate 12 by a locking mechanism 15 that inhibits rotational or axial movement of the screw. As illustrated, a locking mechanism 15 preferably is adjacent each screw hole 19, 20 to secure the screw 14 to plate 12.

Figure 2:
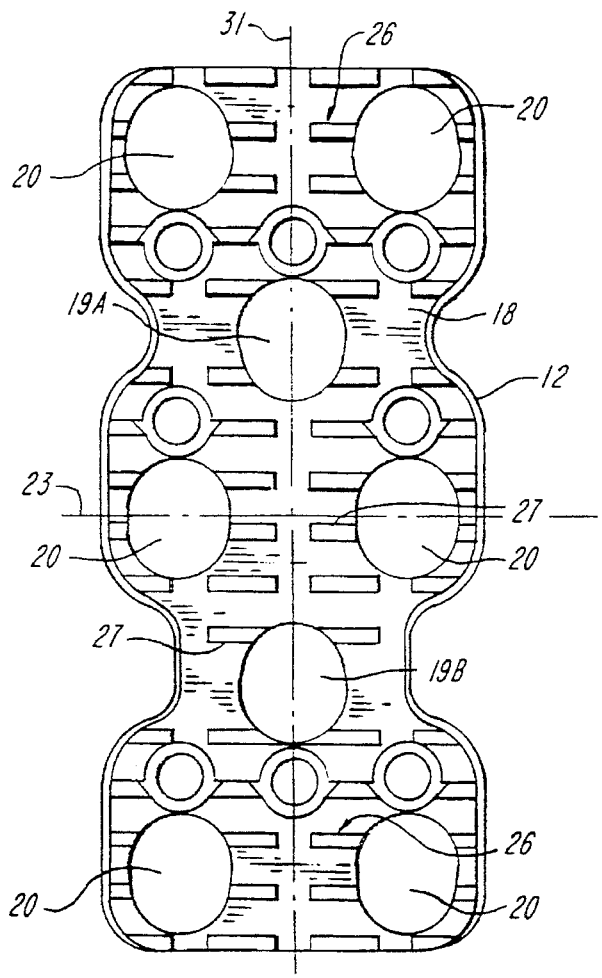
FIG. 2 is a view of the bone contacting surface of the anterior plate of FIG. 1.

FIGS. 2 through 5 further illustrate the osteosynthesis plate system 10 of the invention. As illustrated in FIG. 2, the plate 12 has a textured bone-contacting surface 18 that features a plurality of bone penetrating projections 26. The bone penetrating projections 26 preferably comprise parallel, spaced rows of short protrusions having a triangular or tooth-like shape. The projections 26 are disposed in substantially evenly spaced rows 27 along the long dimension of the plate, with each row preferably extending parallel to the transverse axis 23 of the plate.

As illustrated in FIGS. 4 and 4A the projections 26 are substantially triangular or tooth-shaped objects having acute angles of approximately 60° and 30°. A base 28 is formed by the surface 18 of the plate and a hypotenuse 30 slopes upwardly toward the thickness (or Z) axis midline 32 of plate 18. Preferably the short leg 34 is approximately 0.5 mm in height. The projections preferably are oriented with the cutting edges 29 facing toward the thickness axis midline 32 of the plate.

Figure 3:
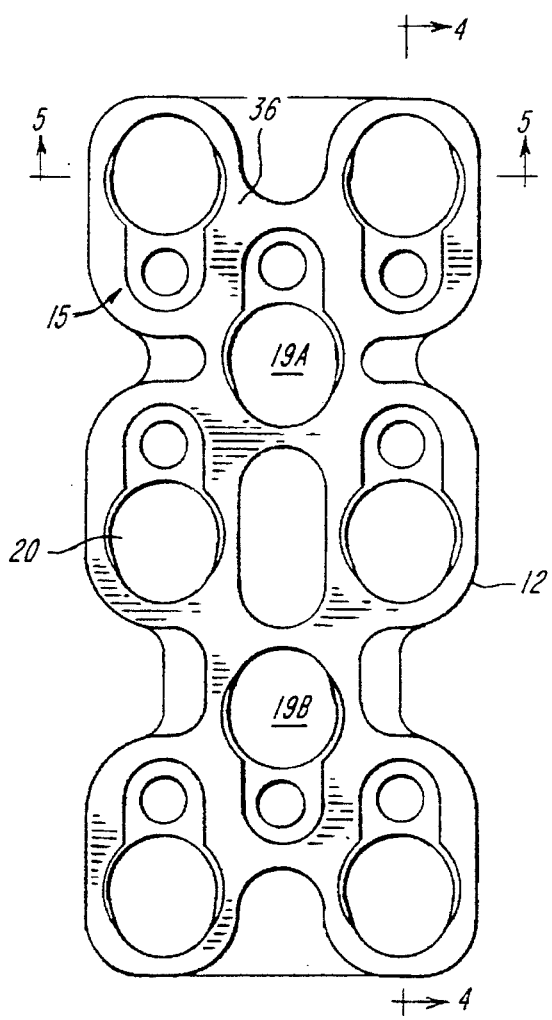
FIG. 3 is a view of the non-bone contacting surface of the anterior plate of FIG. 1.

The non-bone contacting surface 36 of plate 12, as shown in FIG. 3, includes a plurality of screw holes 19, 20 that extend through the plate and which are adapted to seat bone screws. Preferably a locking mechanism 15 is disposed adjacent each screw hole 19, 20. The locking mechanism 15 may comprise a rotatable cam member 24 permanently housed in an aperture 22. The screw holes 19, 20, as illustrated, preferably are substantially circular in shape so as to provide fixed position holes for the placement of screws. The screw holes further have spherical seats, which correspond to a spherical head on the screw, to permit better seating of the screw within the screw hole and infinite angular degrees of freedom in orientation of the screw. The circular screw holes 19, 20 are advantageous as the plates are less prone to longitudinal movement relative to the screws, as sometimes occurs with slot-like or elongate screw holes.

Figure 6A:
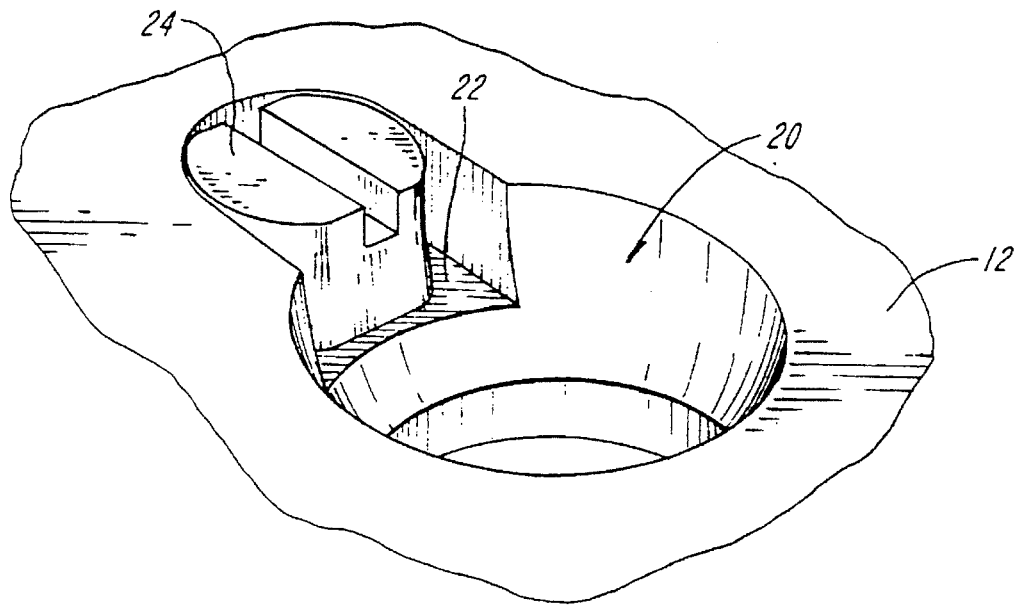
FIG. 6A is a view of a screw locking mechanism useful with the anterior plate of the present invention, in an unlocked position.
Figure 6B:
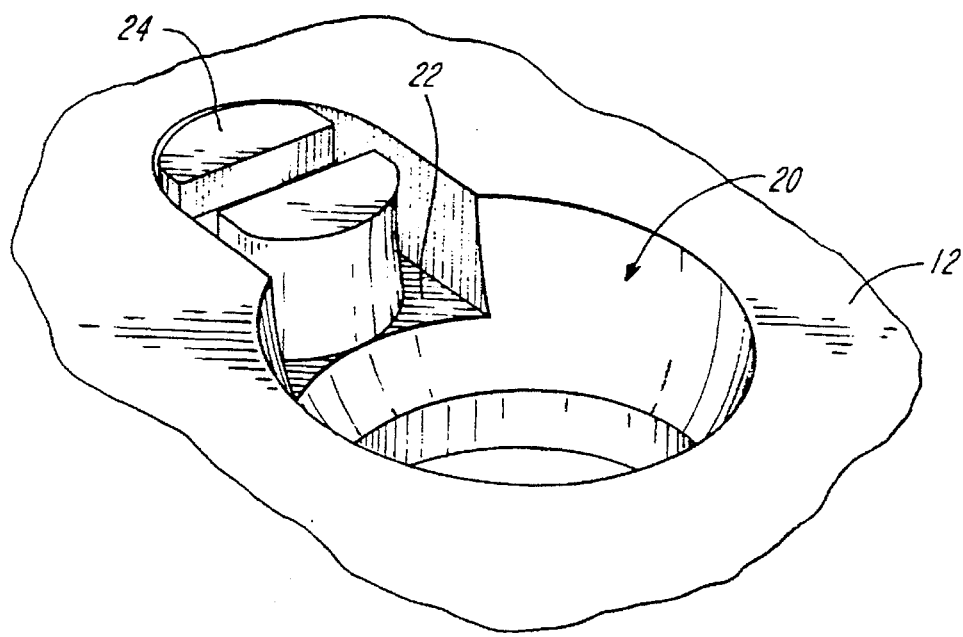
FIG. 6B is a view of a screw locking mechanism useful with the anterior plate of the present invention, in a locked position.

As noted above, the plate system 10 of the invention comprises a locking mechanism 15 that inhibits axial and rotational movement of bone screws 14 once the plate is affixed to vertebral bodies. FIGS. 6A and 6B illustrate one embodiment of the locking mechanism 15 in which a rotatable cam member 24 is permanently housed in an aperture 22 adjacent screw hole 20. With the cam in the unlocked position, as illustrated in FIG. 6A, a screw (not shown) can be inserted into screw hole 20 for anchoring within the bone. Once the screw is fully inserted, cam 24 is then rotated approximately 90°, as shown in FIG. 6B, such that its surface impinges upon a screw inserted in screw hole 20, thus inhibiting rotational and/or axial movement of the screw. Such a locking system integral with the osteosynthesis plate is advantageous in that it does not require a surgeon to manipulate small mechanical parts that must be inserted on the plate for locking. Rather, a permanently installed cam is simply rotated to a locked position to engage the screw.

Figure 7A:
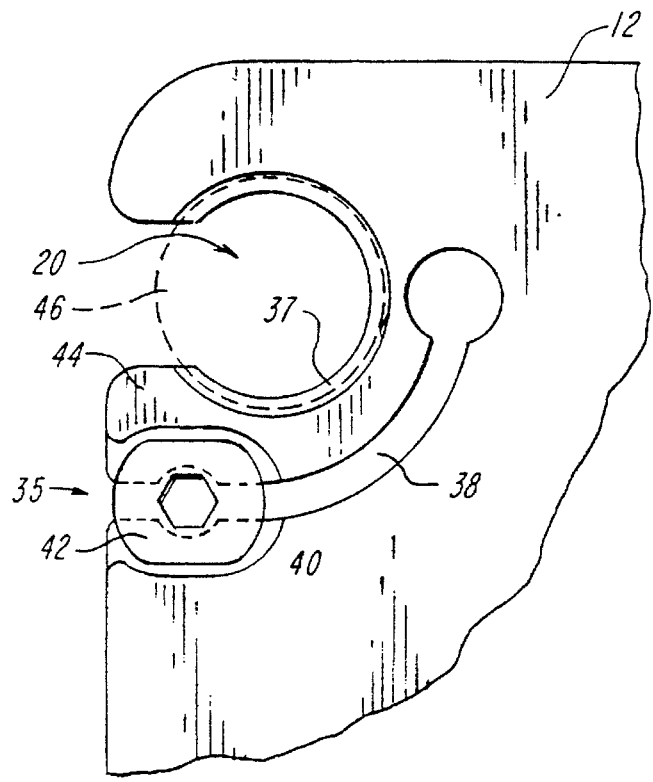
FIG. 7A is a view of another embodiment of a screw locking mechanism useful with the plate of the present invention, in an unlocked position.
Figure 7B:
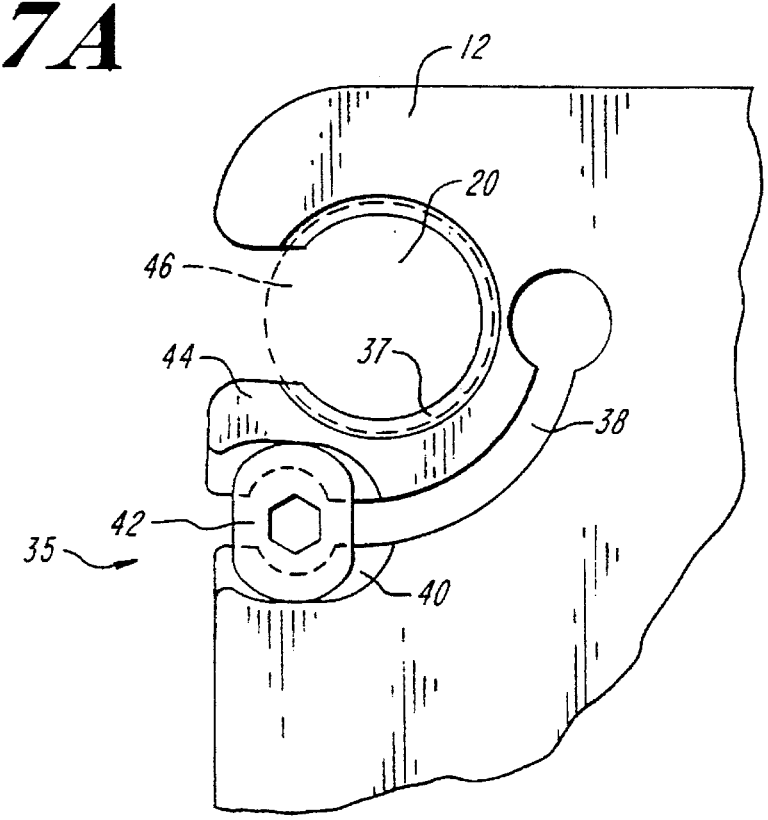
FIG. 7B is a view of another embodiment of a screw locking mechanism useful with the plate of the present invention, in a locked position.

FIGS. 7A and 7B illustrate a locking mechanism 35 which forms another embodiment of the invention. The locking mechanism comprises screw hole 20 adapted to receive a bone screw (not shown) and a rotatable cam 42 permanently housed in aperture 40. A portion 37 of the wall of screw hole 20 forms a deflectable arm 44. Adjacent arm 44 is an arcuate slot 38 that connects with aperture 40.

As shown in FIG. 7A, the locking mechanism 35 is in the unlocked position. In this position a screw may be inserted into the screw hole 20 and affixed to bone. Once fully affixed, cam 42 is rotated approximately 90° to a locked position, as shown in FIG. 7B, thereby exerting a force on deflectable arm 44. The force exerted by cam 42 on arm 44 causes the arm 44 to impinge upon a screw head 46 mounted in screw hole 20 to inhibit axial and rotational movement of the screw.

As noted, cam members 24, 42 preferably are permanently installed on the plate. This can be accomplished in a variety of ways readily understood by one having ordinary skill in the art. For example, the cam can have a stem with a tubular rivet at one end enabling the cam to be staked onto the plate.

The plate 12 preferably is constructed so as to conform to the shape of the anterior surfaces of the vertebrae that it will be mounted upon. Ideally, upon compression of the plate to the bone through the action of bone screws, the bone penetrating projections 26 will become embedded within the cortical layer of bone and the bone contacting surface 18 will be substantially flush against a major portion of the bone segments. The penetration of projections 26 within bone is beneficial in that it affords a more secure fit of the plate to the bone. Moreover, it is believed that the contact of projections 26 with the periosteum may provide sufficient antagonism to evoke a healing response, which may enhance the formation of the solid fusion mass.

As illustrated in FIGS. 4 and 5, the plate 12 is curved along both its longitudinal and transverse axes such that the bone contacting surface 18 is concave. This configuration of the plate 12 is advantageous to enable the plate to conform to the shape of the vertebrae. In a preferred embodiment, the length of the plate 12 along the longitudinal axis preferably results from extending an arc from a minimum of about 7° to a maximum of 25° along an 8.0 inch radius. The width of the plate along the transverse axis preferably results form extending an arc of approximately 52° along a 0.75 inch radius.

Plate 12 is intended to be positioned with its longitudinal axis 31 colinear with the spinal midline, and to be mounted on the anterior surface of the vertebral bodies. Ideally, the longitudinal length of the plate will be sufficient to completely cover the anterior surface of the vertebral bodies from the top front edge of the most cephalad body to the lower front edge of the most caudal body. The length of the plate as well as the number of screw holes in the plate will, of course, vary depending upon the number of vertebral bodies to be fused. The plate illustrated in FIGS. 1 through 3 is intended to span three vertebral bodies and includes three pairs of adjacent, longitudinally spaced screw holes in which each member of the pair is disposed on one side of the longitudinal midline of the plate 12. Further, the plate preferably includes two screw holes 19A, 19B disposed on the longitudinal midline of the plate and on opposite sides of the transverse midline of the plate. Holes 19A, 19B are intended for use in securing optional bone graft pieces placed between adjacent vertebral bodies.

While the plate 12, illustrated and described above, is adapted to span three vertebral bodies, plates may be designed to span anywhere from two to four vertebral bodies. The dimensions of plates intended to span a greater number of vertebral bodies as well as the number of screw holes to be placed in such plates will be readily understood by one having ordinary skill in the art. For example, a plate intended to secure two vertebral bodies can have a length of about 24 to 36 mm with four bone screw holes and one graft screw hole. Similarly, a plate intended to secure three vertebral bodies can have a length of about 38 to 54 mm with 6 bone screw hoes and two graft holes.

Figure 8:
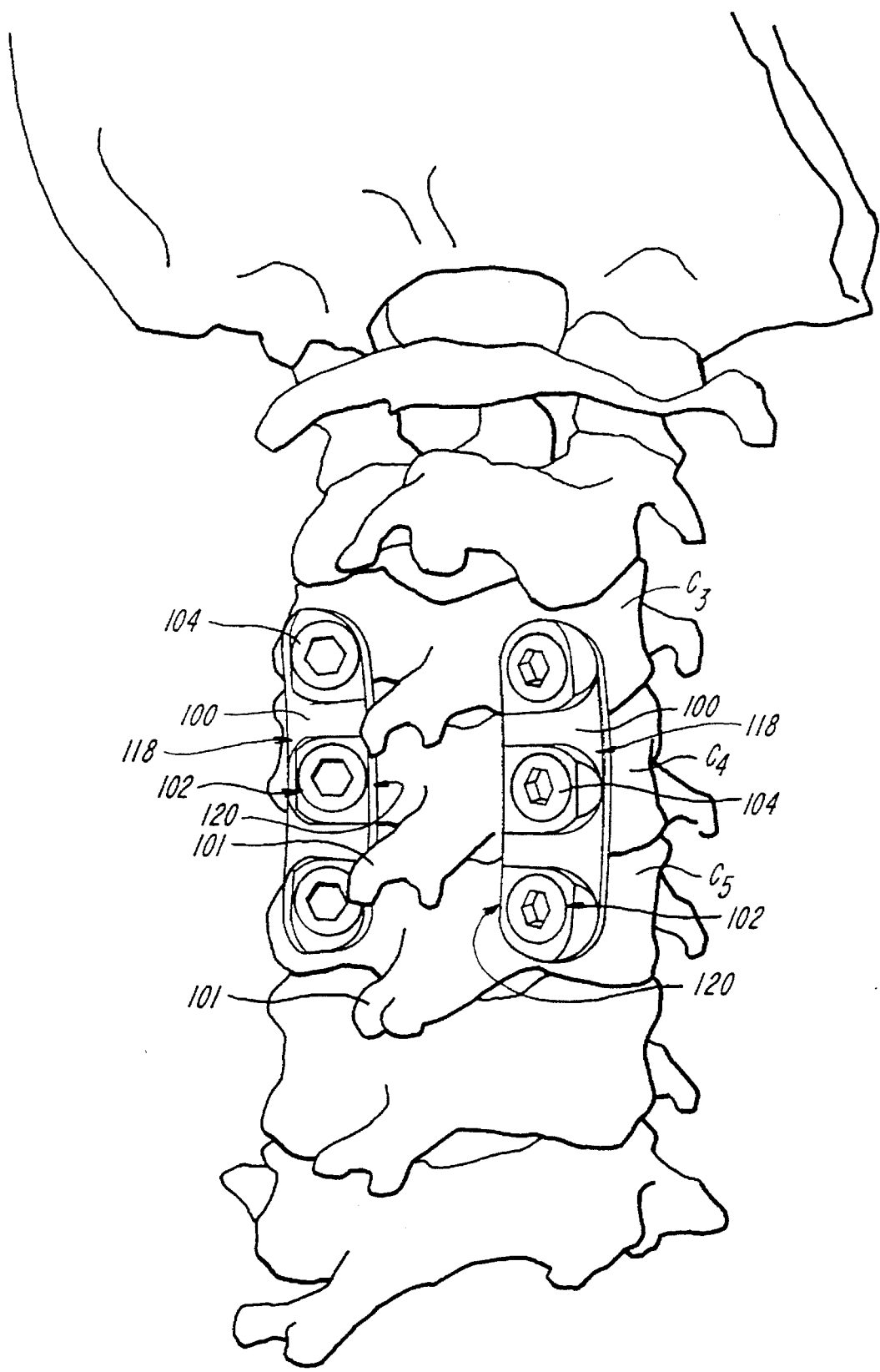
FIG. 8 illustrates a pair of posterior osteosynthesis plates of the present invention affixed to the posterior surface of the cervical spine.

FIG. 8 illustrates a pair of osteosynthesis plates 100, affixed to the posterior surfaces of and fusing the $C_3$, $C_4$ and $C_5$ cervical vertebrae. As illustrated, the osteosynthesis plates 100 intended for mounting on the posterior surface of vertebral bodies are designed to be used in pairs, mounted on the lateral masses of the vertebrae on either side of the spinous process 101. The longitudinal axes of plates 100 are substantially parallel to the spinal midline. Ideally the plates' longitudinal length will be sufficient to completely cover the surface of the lateral mass and facets, from the superior edge of the most cephalad body to the inferior edge of the most caudal body. Each plate 100 has a plurality of screw holes 102, each adapted to receive a bone screw 104, which is adapted to be affixed within the lateral mass of one vertebral body to be joined. The screw holes 102 preferably are aligned along the longitudinal axis of the plate 100.

Figure 9:
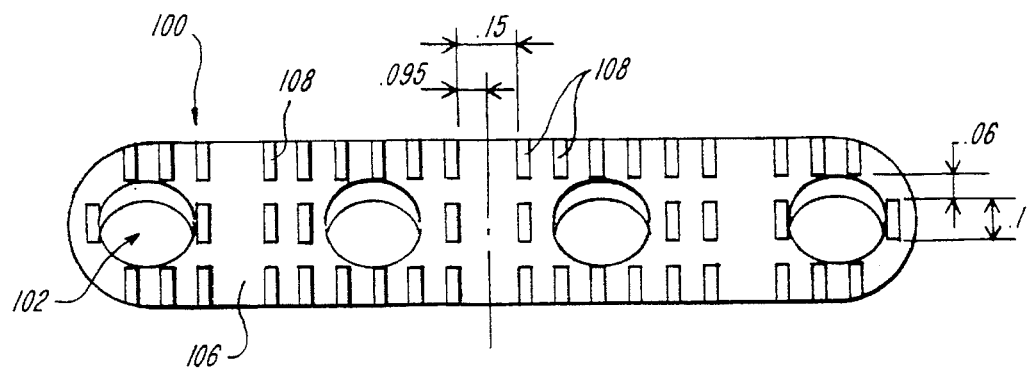
FIG. 9 illustrates the bone contacting surface of a posterior osteosynthesis plate of the present invention.
Figure 10A:
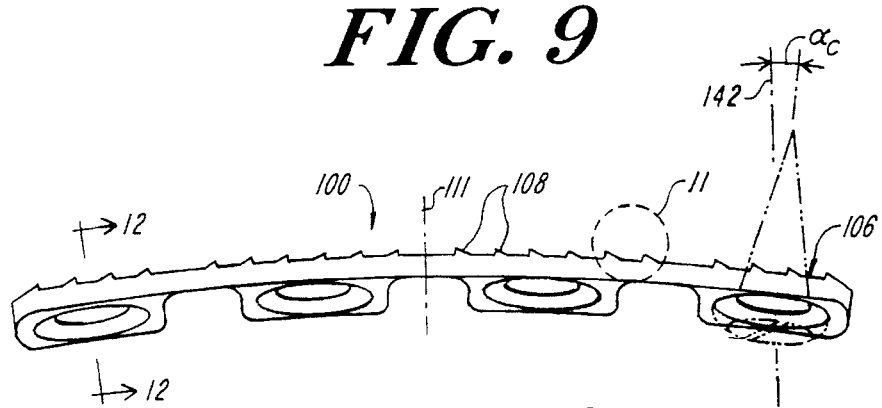
FIG. 10A is a side view of the plate of FIG. 9.
Figure 10B:
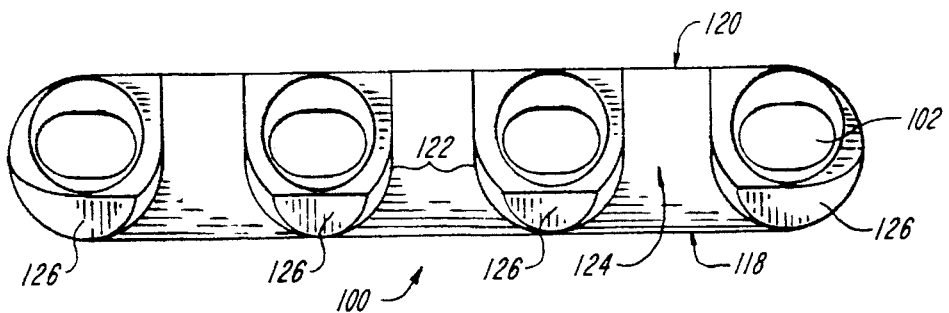
FIG. 10B is a view of the non-bone contacting surface of the plate of FIG. 10A.
Figure 11:
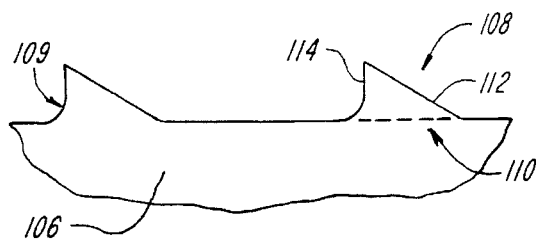
FIG. 11 is a detailed view of area B of FIG. 10A.

The bone-contacting surface 106 of the posterior plate 100, as illustrated in FIGS. 9–11, features a textured surface. The surface 106 has a plurality of parallel, spaced rows of short protrusions 108 which are triangular or tooth-like in shape. The tooth-like rows preferably begin on opposite ends of the long dimension of the plate 100 and recur in spaced intervals toward the center of the plate. The protrusions 108 are oriented with their cutting edges 109 facing toward the thickness (or Z) axis midline 111 of the plate 100. As illustrated in FIGS. 10A and 11, each protrusion 108 is shaped substantially as a right triangle having a base 110 corresponding to the bone-contacting surface 106 and a hypotenuse which extends upwardly toward the thickness axis midline 111 of the plate 100. The short leg 114 has a height of approximately 0.5 mm and faces toward the thickness axis midline 111 of the plate 100.

Protrusions 108 are designed to penetrate the cortical layer of the vertebral bodies upon a compressive force induced by the bone screws 104 when anchored to bone. When a plate 100 is installed, the embedded teeth provide a foothold to better enable the plate to resist migration during translation and rotation. Moreover, the bone-contacting surface 106 should lie substantially flush with the vertebral body when the plates 100 are installed and protrusions 108 are embedded in bone.

Screw holes 102, as illustrated in FIGS. 9 and 10, are substantially circular in shape and preferably are slots with hemicircular ends. Screw holes 102 have spherical countersinks to prevent translation of the bodies through plate slippage. The holes 102, as noted above, are aligned in the longitudinal axis of the plate. Screw holes 102 may be of other shapes as well, including ovoid and elliptical.

Referring to FIGS. 8 and 10A through 13B, the plate 100 has a lateral side 118 and a medial side 120. Each screw hole 102 preferably has a substantially wedge-shaped transverse cross section. The wedge shape of the screw holes 102 can be achieved by each hole 102 being formed in a wedge-like protrusion 122 integrally formed on the dorsal (non-bone contacting) surface 124 of plate 100. For screw holes adapted to seat a bone screw to be anchored at the $C_3$ to $C_7$ vertebrae, the wedge-like protrusion 122 has a raised portion 126 on the lateral side 118 of the plate which tapers to the medial side 120 of the plate. The screw holes 102 are formed angularly in the wedge-like protrusion 122 such that screws may be seated in the vertebral bodies at an optimal angle.

The plates 100 illustrated in FIGS. 10A, 10B, and 12 are intended for mounting upon cervical vertebrae 3 through 7.

The screw holes 102 formed in such plates preferably should have a cephalad angle ($\alpha_c$) of orientation of approximately 15°. Similarly, the wedge shaped protrusion 122 enables screw holes 102 to be formed at a lateral angle ($\alpha_C$) of about 20°. Accordingly, bone screws intended to be anchored in the $C_3$ to $C_7$ vertebrae will preferably enter the vertebral body projecting in the cephalad direction at an angle of about 15° relative to the thickness axis 142 of each hole. The screw also projects in the lateral direction at an angle of 20° relative to the thickness axis 142 of each hole.

FIGS. 13A, 13B and 14 illustrate a plate having one screw hole 116 specially adapted to seat a screw intended to be anchored in the $C_2$ vertebra. Screw holes 128, 130, and 132 are constructed as described above and are intended to seat screws to be anchored in the $C_3$, $C_4$ and $C_5$ vertebrae, respectively.

Due to the morphology of the $C_2$ vertebra, a bone screw should be directed into this vertebral body at a medial and cephalad angle, rather than at a lateral and cephalad angle. Accordingly, the wedge-like protrusion 134 within which hole 116 can be formed having a raised medial side 136 and a raised cephalad side 138. The geometry of hole 116 enables a bone screw to project into the lateral mass of the $C_2$ vertebra in the cephalad direction at an angle ($\alpha_c$) of about 25° relative to the thickness axis 142 of each hole. The plate also projects in the medial direction at an angle ($\alpha_m$) of about 10° relative to the thickness axis 142 of each hole.

FIGS. 10A, 12, 13A and 14 illustrate the desired curved geometry of the bone contacting surface 106 of the plate 100 that maximizes the ability of the plate to conform to the shape of the posterior surfaces of the cervical vertebrae. Preferably, the plate 100 is curved about its longitudinal axis such that the bone contacting surface is convex, and about its transverse axis such that bone contacting surface 106 is concave. In a preferred embodiment the longitudinal curve of plate 100 is along an arc of about a 165 mm radius. The plate preferably has a transverse curve along an arc of a 22 mm radius. One skilled in the art will readily appreciate that the curve of the plate in both the longitudinal and transverse axis may be modified to improve its conformity to the shape of the vertebrae bodies.

Figure 15A:
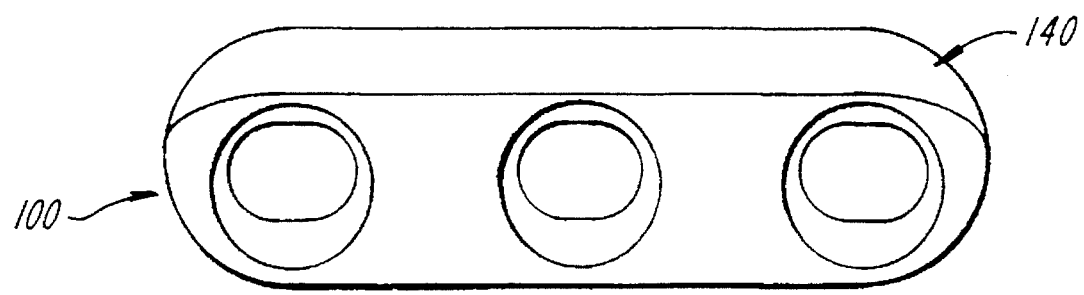
FIG. 15 is a view of the non-bone contacting surface of an alternative embodiment of a posterior plate.
FIG. 15B is a side view of the plate illustrated in FIG. 15A.
Figure 15B:
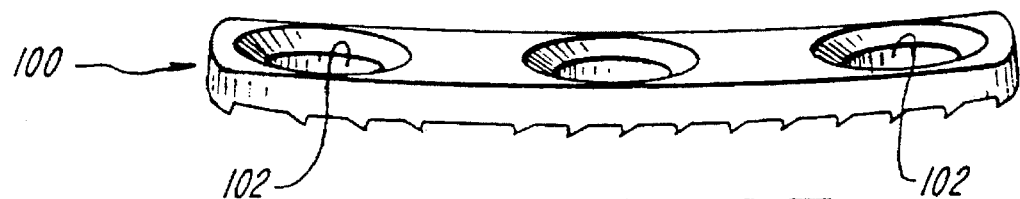

FIGS. 15A and 15B illustrate an alternative embodiment of plate 100, having a thicker profile. The plate 100 illustrated in FIGS. 15A and B has a thickened, or raised lateral side 140, which replaces the individual wedge-like protrusions surrounding each screw hole 102 as in FIGS. 8 through 14.

Plate 100 illustrated herein has four screw holes and is adapted to fuse four vertebrae. Plates can be designed with a greater or lesser number of screw holes to fuse more or less vertebral bodies. Typically, plates can have between about two and five screw holes each for fusing from two and up to five vertebrae.

One of ordinary skill in the art will appreciate that the plates 12, 100 of the invention can be made of a variety to high strength, biologically compatible materials that preferably are compatible with MRI techniques. Useful materials include polymers, stainless steel, titanium and titanium alloys. A currently preferred material is a titanium-aluminum alloy having 90% titanium and 6% aluminum, and 4% vanadium.

Various modifications may be made to the plate system of the invention without exceeding the intended scope of the claims. For example, the bone penetrating projections may assume a different geometry and may be oriented so as to be parallel with the longitudinal axis of the plates.

What is claimed is:

1. An osteosynthesis plate system, comprising
a rigid, elongate plate member adapted to mount upon the posterior surfaces of two or more vertebral bodies to bridge and immobilize adjacent vertebral bodies, the member having a first, bone contacting surface and a second, non-bone contacting surface and the member being curved such that the first surface is concave in the transverse axis of the member, with the apex of the concavity being in the direction of the second surface, and convex in the longitudinal axis of the member such that the first surface is capable of contacting two or more vertebral bodies upon which the plate member is mounted;

at least two screw holes having substantially spherical countersinks and each being adapted to receive a bone screw, the holes being in substantial alignment with one another about the longitudinal axis of the member and being oriented at an angle in the cephalad direction in the range of 15° to 25° and at an angle in the medial or lateral directions in the range of 10° to 20° relative to a thickness axis of the member running from the first surface to the second surface to ensure proper positioning of the bone screw within the hole at a desired cephalad angle and at a desired medial or lateral angle relative to the thickness axis of the member, angular orientation of the screw holes in the medial direction being achieved by a wedge-shaped protrusion integrally formed on the medial side of the plate adjacent each of the screw holes and angular orientation of the screw holes in the lateral direction being achieved by a wedge-shaped protrusion formed on the lateral side of the plate adjacent each of the screw holes; and a plurality of bone penetrating projections disposed on the first surface of the member.

2. The plate system of claim 1 wherein the member is adapted to mount upon the posterior surface of the vertebral bodies, adjacent to the spinous process thereof, and the member has between 2 and 5 screw holes, each being adapted to guide a bone screw into the lateral mass of a vertebral body, with one bone screw positioned within each vertebra being fused.

3. The plate system of claim 1 wherein the bone penetrating projections are formed of discontinuous structures, each extending traverse to the longitudinal axis of the member.

4. The plate system of claim 3 wherein each structure has a substantially triangular cross section.

5. The plate system of claim 4 wherein a cutting surface of each structure faces toward the thickness axis midline of the member.

6. An osteosynthesis plate system, comprising
a rigid, elongate plate member adapted to mount upon the posterior surfaces of two or more vertebral bodies to bridge and immobilize adjacent vertebral bodies, the member having a first, bone contacting surface and a second, non-bone contacting surface and the member being curved such that the first surface is concave in the transverse axis of the member, with the apex of the concavity being in the direction of the second surface, and convex in the longitudinal axis of the member such that the first surface is capable of contacting two or more vertebral bodies upon which the plate member is mounted;

at least two screw holes having substantially spherical countersinks and each being adapted to receive a bone screw, the holes being in substantial alignment with one another about the longitudinal axis of the member and being oriented at an angle in the cephalad direction in the range of 15° to 25° and at an angle in the medial or lateral directions in the range of 10° to 20° relative to a thickness axis of the member running from the first surface to the second surface to ensure proper positioning of the bone screw within the hole at a desired cephalad angle and at a desired medial or lateral angle relative to the thickness axis of the member;

a plurality of bone penetrating projections disposed on the first surface of the member; wherein the member is adapted to mount upon the posterior surface of the vertebral bodies, adjacent to the spinous process thereof and the member has between 2 and 5 screw holes, each being adapted to guide a bone screw into the lateral mass of a vertebral body, with one bone screw positioned within each vertebra being fused; and wherein the member is adapted to join at least two adjacent cervical vertebrae from the third to the seventh cervical vertebrae, and the screw holes are angularly oriented within the member such that a bone screw inserted within the screw hole will project in the cephalad direction at an angle of about 15° relative to the thickness axis of the hole and in the lateral direction at an angle of about 20° relative to the thickness axis of the hole.

* * * * *